United States Patent
Capovilla et al.

(10) Patent No.: US 11,541,433 B2
(45) Date of Patent: Jan. 3, 2023

(54) CONTAINING DEVICE FOR A TREATMENT MACHINE, IN PARTICULAR A WASHING AND/OR STERILIZATION MACHINE, FOR LOOSE PRODUCTS

(71) Applicant: ICOS PHARMA S.P.A., Zappola (IT)

(72) Inventors: Ivone Capovilla, Loria (IT); Ottorino Casonato, Castelfranco Veneto (IT); Fabio Zardini, Castelfranco Veneto (IT)

(73) Assignee: ICOS PHARMA S.P.A., Zappola (IT)

( * ) Notice: Subject to any disclaimer, the term of this patent is extended or adjusted under 35 U.S.C. 154(b) by 722 days.

(21) Appl. No.: 15/458,493

(22) Filed: Mar. 14, 2017

(65) Prior Publication Data

US 2017/0260677 A1    Sep. 14, 2017

(51) Int. Cl.
| | | |
|---|---|---|
| B08B 3/06 | (2006.01) | |
| B08B 3/04 | (2006.01) | |
| B65D 43/16 | (2006.01) | |
| B65D 6/08 | (2006.01) | |
| A61L 2/26 | (2006.01) | |
| D06F 21/04 | (2006.01) | |
| A61L 2/18 | (2006.01) | |
| A61L 2/20 | (2006.01) | |

(52) U.S. Cl.
CPC ............ *B08B 3/045* (2013.01); *A61L 2/26* (2013.01); *B08B 3/047* (2013.01); *B08B 3/06* (2013.01); *B65D 7/16* (2013.01); *B65D 43/161* (2013.01); *D06F 21/04* (2013.01); *A61L 2/18* (2013.01); *A61L 2/20* (2013.01); *A61L 2202/122* (2013.01); *A61L 2202/17* (2013.01)

(58) Field of Classification Search
None
See application file for complete search history.

(56) References Cited

U.S. PATENT DOCUMENTS

| | | | | |
|---|---|---|---|---|
| 3,478,193 A | * | 11/1969 | Molitor ................. | A47B 31/02 219/386 |
| 4,370,992 A | * | 2/1983 | Choudhury ............... | B08B 3/00 134/100.1 |
| 5,907,961 A | * | 6/1999 | Lee .......................... | D06B 3/30 68/140 |
| 6,374,644 B1 | * | 4/2002 | Rhode ..................... | D06F 37/08 24/58 |

(Continued)

FOREIGN PATENT DOCUMENTS

| | | |
|---|---|---|
| EP | 2275018 A2 | 1/2011 |
| WO | WO-201515058 A1 | 10/2015 |

*Primary Examiner* — Mikhail Kornakov
*Assistant Examiner* — Ryan L Coleman
(74) *Attorney, Agent, or Firm* — Marshall, Gerstein & Borun LLP

(57) ABSTRACT

Containing device for a treatment machine for loose products, provided internally with a treatment compartment that has at least an open side for loading the loose products to be treated, and for unloading the loose products that have been treated; the containing device comprises at least a first loading door for the loose products to be treated, positioned on a first portion of said open side and associated with at least a respective opening and closing unit, and at least a second unloading door for the loose products that have been treated, positioned on a second portion of said open side and associated with at least a respective opening and closing unit.

15 Claims, 5 Drawing Sheets

(56) References Cited

U.S. PATENT DOCUMENTS

2005/0081898 A1* 4/2005 Williams .................. B62B 3/02
134/172
2015/0023839 A1* 1/2015 Snyder ...................... A61L 2/07
422/28

* cited by examiner

CONTAINING DEVICE FOR A TREATMENT MACHINE, IN PARTICULAR A WASHING AND/OR STERILIZATION MACHINE, FOR LOOSE PRODUCTS

FIELD OF THE INVENTION

The present invention concerns a containing device for loose products suitable for a machine for treating them, for example washing and/or sterilizing them, and usable for example in the pharmaceutical field, hospitals, the food industry or in the industrial field, in the production of loose products.

The loose products can be, for example, closing stoppers for test tubes for laboratory analysis, closing stoppers for phials of medicines, or small instruments or objects used in operating theaters or laboratories.

The present invention also concerns a treatment method and machine, for example washing and/or sterilization, for loose products, in which, in particular, the zones where the loose products are loaded and unloaded are positioned on the same side.

BACKGROUND OF THE INVENTION

It is known, in the pharmaceutical field, in hospitals or other fields, for example the food industry, that it is necessary to treat, for example wash and/or sterilize, loose products in washing and/or sterilization machines provided with a sealed treatment chamber, delimited by walls, in which a rotary drum receives the loose products to be treated on a loading side, washes and/or sterilizes them during a treatment cycle, and unloads them on an unloading side, where they are generally packaged in sterile packages.

The rotary drums of these machines are partitioned by a multitude of containing devices, such as for example angular containing sectors, each able to contain, with every operating cycle, a desired quantity of loose products to be treated. The containing devices are normally in the form of racks, so as to guarantee an efficient washing and/or sterilization treatment.

Among the loose products that are normally treated we can include for example stoppers for closing test tubes intended to contain substances to be subjected to laboratory analysis, closing stoppers for phials of medicines or generally for containers of medicines, or small instruments or objects used in operating theaters or laboratories. The materials they can be made of include, by way of example, rubber, plastic, polymer materials, metals or metal alloys.

The loose products to be treated are loaded, through a first aperture provided with a door and manually or automatically inside the containing devices in order to carry out the treatment, for example washing and/or sterilization. Once the loose products have finished their treatment, they are unloaded through a second aperture, communicating for example with an unloading valve.

As is also known, machines for treating loose products exist which have the first loading aperture for the loose products to be treated and the second aperture for unloading the treated products on the same side; these machines are therefore very compact, efficient and particularly suitable for use in spaces that have to be limited.

However, such machines, with the loose products loaded and unloaded on the same side, can have problems of blockages and the accumulation of loose products, in particular during the loading and/or unloading of the loose products. Moreover, the loose products could remain trapped in an unwanted manner inside the containers, or even escape from the containing device during the treatment process.

The accumulation of loose products can occur for example in the bottom of the containing devices which, as we said, can be in the shape of angular sectors.

Document EP 2275018 A2 describes a machine for treating loose products, in particular for washing them, provided with a device to contain the loose products.

Document WO 2015150581 A1 describes a machine for sterilizing loose products.

However, these machines also suffer from the same problems as the known machines cited above, and in particular have obvious limitations, in particular in the steps of loading and unloading the loose products.

Other limitations and disadvantages of conventional solutions and technologies will be clear to a person of skill after reading the remaining part of the present description with reference to the drawings and the description of the embodiments that follow, although it is clear that the description of the state of the art connected to the present description must not be considered an admission that what is described here is already known from the state of the prior art.

There is therefore a need to perfect a containing device for loose products for treatment, in particular washing and/or sterilization of the loose products, and corresponding machine and method, which can overcome at least one of the disadvantages of the state of the art.

In particular, one purpose of the present invention is to obtain a containing device for loose products, particularly suitable for machines for treating loose products with the loading and unloading of the loose products on the same side, which prevents any risk of blockage and/or accumulation of loose products both in the loading step and also in the unloading step.

Another purpose of the present invention is to obtain a containing device for loose products which, in the unloading of the loose products that have been treated, has an unloading area which is totally without any obstacle, therefore by means of which the loose products can be conveyed due to gravity, rapidly and efficiently toward an unloading zone of the machine.

Another purpose of the present invention is to obtain a containing device for loose products which prevents the loose products from escaping accidentally and unwantedly during any step of their treatment inside the drum.

Another purpose of the present invention is to obtain a treatment machine for loose products provided with loading and unloading zones of the loose products situated on the same side, which allows rapid and efficient operations to load and unload the loose products.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, a containing device, suitable to house loose products, is provided internally with a treatment compartment that has two flat and opposite lateral walls, connected by two other lateral walls; wherein said two flat and opposite lateral walls and said two other lateral walls are connected in correspondence with their lower sides by means of a bottom wall and form on their upper sides at least one open side to load the loose products to be treated and to unload the loose products that have been treated; and wherein the planes on which said two flat and opposite lateral walls lie are reciprocally symmetrical with respect to a plane, so that said planes converge on a line positioned on the other side of the bottom wall with respect to the open side; whereby the containing device comprises at least a first loading door for the loose products to be treated, positioned on a first portion of said open side and associated with at least a respective opening and closing unit, and at least a second unloading door for the loose products that have been treated, positioned on a second portion of said open side and associated with at least a respective opening and closing unit.

According to one aspect of the invention, the loading door and the unloading door are connected to the containing device by means of corresponding rotation pins that allow said doors to rotate around said rotation pins, whereby said rotation pins are situated nearer to each other than to any of said flat and opposite lateral walls.

The present invention also concerns a machine to treat loose products, comprising a treatment chamber in which a rotatable drum is housed, a loading zone for loading the loose products to be treated and an unloading zone for unloading the loose products that have been treated, positioned on the same side of the machine, in which the drum comprises a plurality of containing devices as defined above.

The invention also concerns a method for treating loose products in a treatment machine for loose products, where the machine comprises a treatment chamber in which a rotatable drum is housed, a loading zone for loading the loose products to be treated and an unloading zone for unloading the loose products that have been treated, positioned on the same side of the machine, the drum comprises a plurality of containing devices as defined above and provided internally with a treatment compartment that has at least one open side for loading the loose products to be treated and for unloading the loose products that have been treated.

According to one aspect of the invention, the method comprises loading the loose products to be treated in said treatment compartment of each of the containing devices through a loading door positioned on a first portion of the open side of the treatment compartment of each of the containing devices, treating said loose products by rotating the drum, and unloading the loose products that have been treated from each of said containing devices by means of an unloading door positioned on a second portion of said open side of the treatment compartment of each of the containing devices.

These and other aspects, characteristics and advantages of the present disclosure will be better understood with reference to the following description, drawings and attached claims. The drawings, which are integrated and form part of the present description, show some embodiments of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some embodiments, given as a non-restrictive example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION

Figure 1:
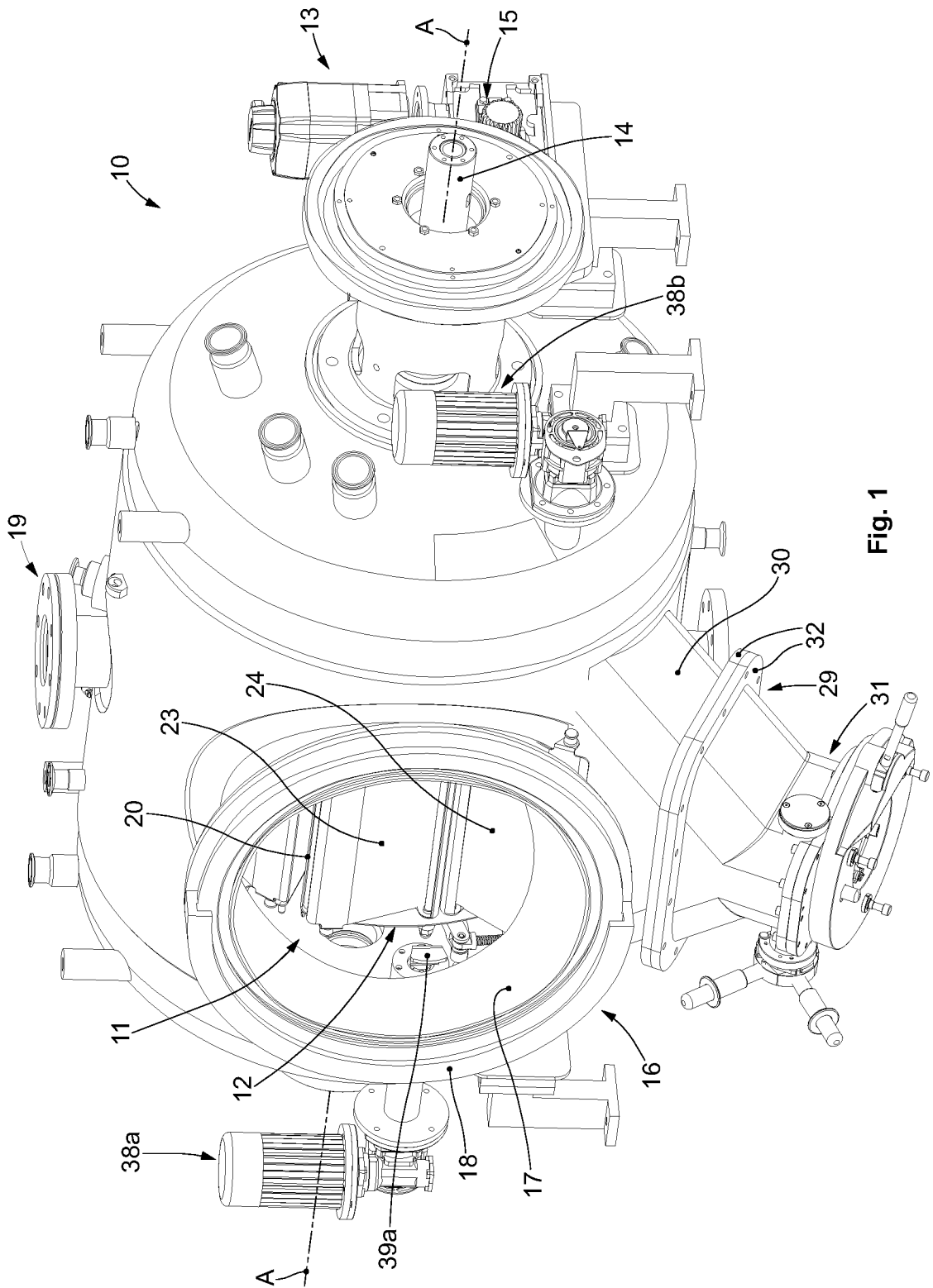
FIG. 1 is a three-dimensional view of a treatment machine for loose products, for example washing and/or sterilization, according to the present invention.

We shall now refer in detail to the various embodiments of the present invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

With reference to the attached drawings, a machine 10 for treating loose products, for example washing and/or sterilizing loose products, comprises a treatment chamber 11 inside which a rotatable drum 12 is housed.

The drum 12 can be made to rotate around an axis A by means of a drive device 13 which, through a transmission unit 15, makes a shaft 14 rotate which is suitably integrated with the drum 12. The axis of rotation A is preferably the longitudinal axis of the machine.

The drum 12 (see FIG. 5 for example) is provided with a plurality of containing devices 20 for the loose products to be treated.

The machine 10 (see FIGS. 1 and 2 for example), comprises a first loading zone 16 of the loose products, in particular a manual loading zone, provided with a loading aperture 17 associated with a loading door 18, able to allow the manual loading of the loose products inside the drum 12.

The machine 10 also comprises a second loading zone 19 of the loose products, in particular an automatic loading zone, in which a pneumatic loading apparatus can be provided for example, for loading the loose products into the drum 12.

The machine 10 comprises an unloading zone 29 of the loose products that have been treated inside the containing devices 20 of the drum 12.

The unloading zone 29 comprises an unloading pipe 30, situated in a lower part of the treatment chamber 11. The unloading pipe 30 faces at a first end toward the containing devices 20 of the drum 12, and is connected, at the opposite end, with an unloading valve 31. The connection between the unloading pipe 30 and the unloading valve 31 can be obtained for example by means of a pair of flanges 32.

The loading zone 16 of the loose products to be treated and the unloading zone 29 of the loose products that have been treated (see FIGS. 2 and 5 for example, relating to lateral views considered from the two opposite sides of the machine 10), are positioned on the same side of the machine, for example the front side.

The containing devices 20 (see FIG. 3 for example), are in the form of a rack and each comprise a treatment compartment 40 in which the loose products to be treated are introduced.

The treatment compartment 40 is delimited by a bottom wall 21 facing toward the center of the drum 12, hence toward the axis of rotation A of the drum 12.

Each of the containing devices 20 also comprises an open side 22, opposite the bottom wall 21, on which an unloading door 23 is disposed, positioned on a first portion of the open side 22 and suitable to allow the loose products to be treated to be loaded, and also an unloading door 24, positioned on a second portion of the open side 22 and suitable to allow the loose products that have been treated to be unloaded from the containing device 20.

Figure 5:
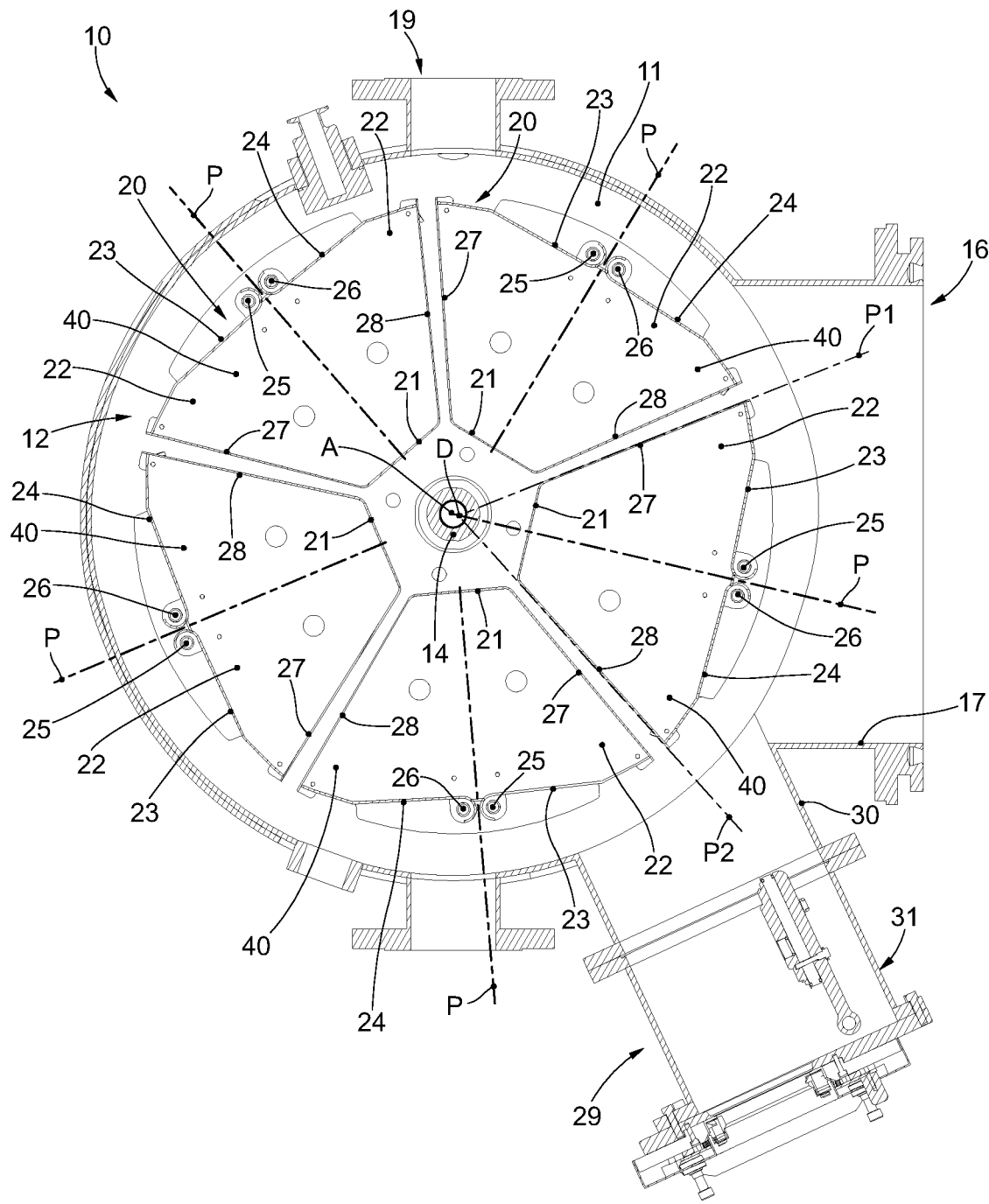
FIG. 5 is a partly sectioned view from a second side of the machine, opposite the first side shown in FIG. 2.

The loading door 23 and the unloading door 24, in the case shown in FIG. 5 in which the containing device 20 is closed, occupy the whole extension of the open side 22 of the containing device 20.

The loading door 23 is rotatable around a first rotation pin 25, while the unloading door 24 is rotatable around a second rotation pin 26.

The first rotation pin 25 and the second rotation pin 26 are positioned in correspondence with a central zone of the open side 22 of the containing device 20.

The loading and unloading doors 23 and 24 can be made of the same size and be disposed specular with respect to a symmetry plane P, in particular a longitudinal plane, of the containing device 20.

The loading and unloading doors 23 and 24 are able to rotate, to open or close, in opposite directions around the corresponding rotation pins 25 and 26.

The treatment compartment 40 of each of the containing devices 20 is completed by first lateral walls 27 and 28, that is to say, an upper wall 27 and a lower wall 28, directed in a longitudinal direction of the machine 10 and the drum 12, hence a direction substantially parallel to the axis A, and by two other lateral walls 41 and 42, positioned in a direction substantially transverse to the axis A.

The upper wall 27 and the lower wall 28, that is, the first lateral walls, are substantially flat and opposite the plane P.

The walls 27 and 28 lie on planes P1 and P2 which converge, together with the plane P, on a determinate line D (see FIG. 5 in particular). The planes P1 and P2 are symmetrical with respect to the plane P.

Line D is situated near axis A and could coincide with axis A. Moreover, the line D could be common to all the containing devices 20.

The rotation pins 25 and 26 are nearer each other that to any of the lateral walls 27 and 28.

As we said, the containing devices 20 are in the form of a rack, therefore at least some of the walls described above and which define the treatment compartment 40 are wholly or partly provided with small holes or suchlike, so that in the containing device 20 the washing and/or sterilization treatment can be efficiently carried out. The loading and unloading doors 23 and 24 can also be provided wholly or partly with small holes.

Preferably the bottom wall 21 is smaller in extension than the open side 22, so that the containing devices 20 have a substantially trapezoid shape of the cross section.

The containing devices 20 can be made as sectors of a circle with the center in the axis A and preferably positioned so that they are adjacent to each other or suitably distanced from each other.

Preferably the containing devices 20 are identical to each other and are positioned at regular intervals around the axis of rotation A of the rotary drum 12.

The drum 12 can comprise any number whatsoever of containing devices 20, however Applicant has found that a particularly effective and productive conformation comprises the disposition of five containing devices 20, as in FIG. 5, which confer on the drum 12 in its entirety a substantially pentagonal shape.

Each of the loading and unloading doors 23 and 24 of each of the containing devices 20 is associated, on both the opposite lateral walls 41 and 42, with a respective opening and closing unit 33a and 33b.

Each pair of opening and closing units 33a is connected to a respective loading door 23, so as to make it selectively assume an open or closed position.

Each pair of opening and closing units 33b is connected to a respective unloading door 24, so as to make it selectively assume an open or closed position.

The loading door 23, in its closed position, is able to abut on pins 43 protruding from the lateral walls 41 and 42, while the unloading door 24, in its closed position, is able to abut on other pins 44 protruding from the lateral walls 41 and 42.

Each opening and closing unit 33a of the loading door 23 comprises a first arm 34a carrying an end part 35a cooperating with the loading door 23, preferably in a zone near the free edge 47 of the loading door 23, that is to say, the edge opposite the rotation pin 25.

The first arm 34a of each of the opening and closing units 33a is connected, by means of an articulation pin 36a, to one end of a second arm 37a, the other end of which is rotatably connected to the rotation pin 25.

Each opening and closing unit 33b of the unloading door 24 comprises a first arm 34b carrying an end part 35b associated with the unloading door 24, preferably in a zone near the free edge 46 of the unloading door 24, that is to say, the edge opposite the rotation pin 26.

The first arm 34b of the opening and closing unit 33b is connected, by means of an articulation pin 36b, to one end of a second arm 37b, the other end of which is rotatably connected to the rotation pin 26.

Figure 3:
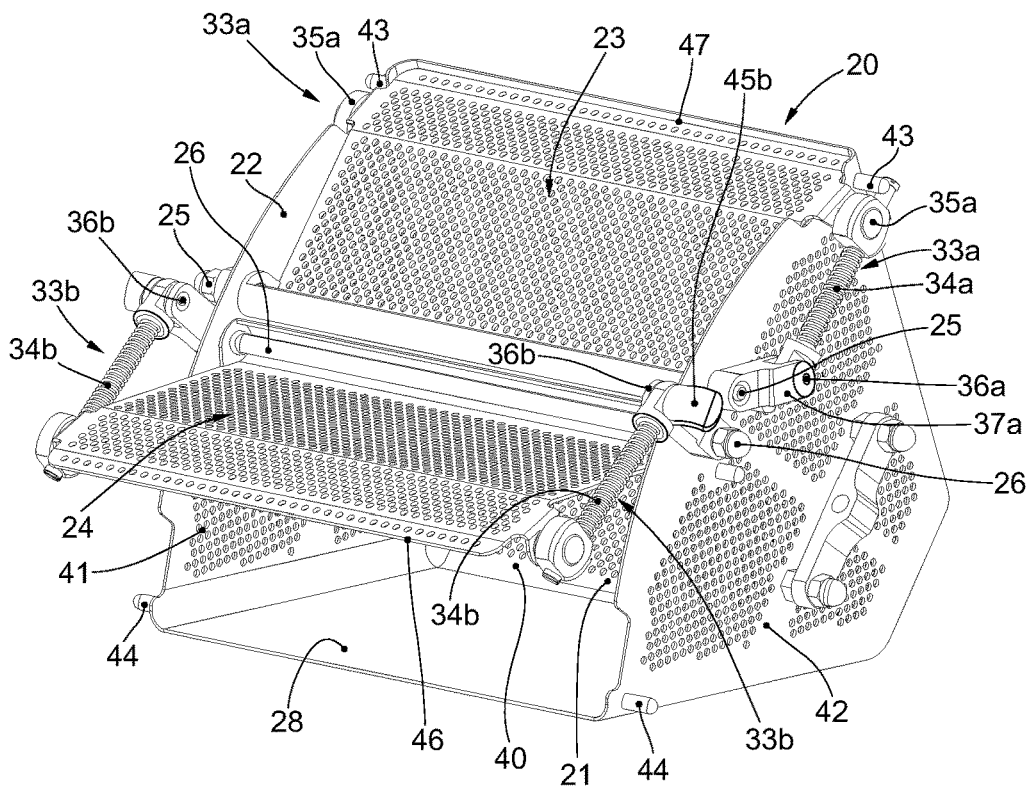
FIG. 3 is a three-dimensional view of a containing device for loose products according to the present invention.

For each pair of the opening and closing units 33b of the unloading door 24, the positioning is provided of at least one pawl 45b, protruding laterally from at least one of said opening and closing units 33b. The pawl 45b is positioned in correspondence with the articulation pin 36b. In the case of FIG. 3, the pawl 45b protrudes from the opening and closing unit 33b of the unloading door 24 situated on the right, looking at the drawing.

In the same way, for each pair of opening and closing units 33a of the loading door 23, the positioning is provided of at least one pawl 45a (see FIG. 6), protruding laterally from at least one of said opening and closing units 33a. The pawl 45a is positioned in correspondence with the articulation pin 36a.

The loading and unloading doors 23 and 24 can be opened by thrusting on the corresponding pawls 45a and 45b of the corresponding opening and closing units 33a and 33b, against the possible action of elastic return elements that tend to keep the loading and unloading doors 23 and 24 in the closed position.

The opening and closing units 33a of the loading doors 23 cooperate, by means of the corresponding pawls 45a, with an actuator 38a comprising a drive element 39a, for example a cam type drive element, which on each occasion can engage with the pawl 45a of an opening and closing unit 33a of the loading door 23 to allow to load the loose products to be treated inside the containing device 20.

The opening and closing units 33b of the unloading doors 24 cooperate, by means of the corresponding pawls 45b, with an actuator 38b comprising a drive element 39b, for example a cam type drive element, which on each occasion can engage with the pawl 45b of the unloading door 24 to allow to unload the loose products that have been treated from the containing device 20.

Figure 4:
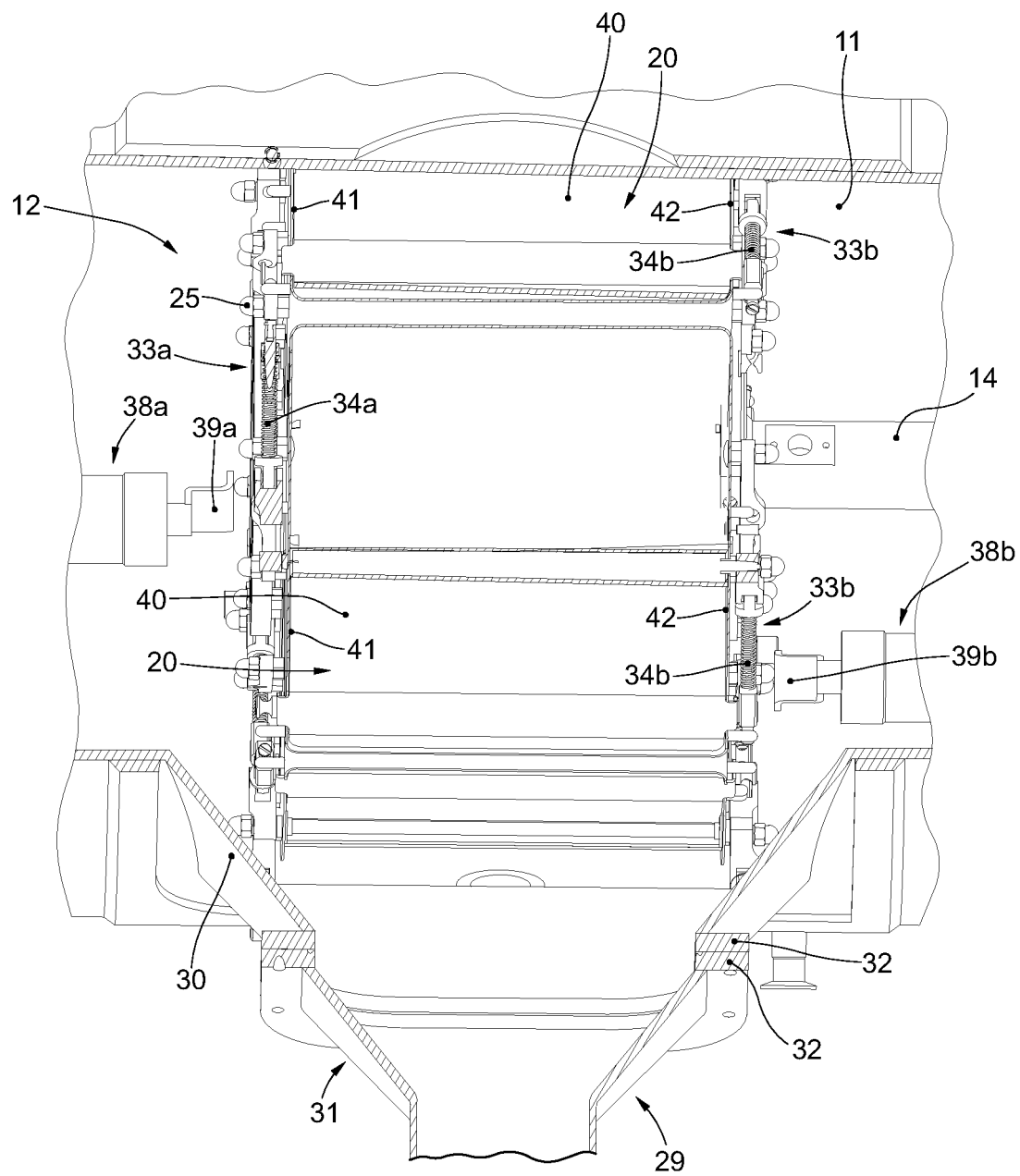
FIG. 4 is a front view in longitudinal section of a central zone of the treatment machine for loose products.

The actuators 38a and 38b are preferably positioned on opposite sides of the machine 10 and the drum 12 (see FIG. 1 or FIG. 4 for example).

The pawls 45a associated with the opening and closing units 33a of the loading doors 23 and the pawls 45b associated with the opening and closing units 33b of the unloading doors 24 are also situated on opposite sides of the containing device 20 and the drum 12.

The drive element 39a of the actuator 38a, in substance, following the rotation of the drum 12, engages on each occasion with a pawl 45a protruding from the opening and closing unit 33a of the loading door 23.

The drive element 39b of the actuator 38b, following the rotation of the drum 12, also engages on each occasion with a pawl 45b protruding from the opening and closing unit 33b of the unloading door 24.

Figure 6:
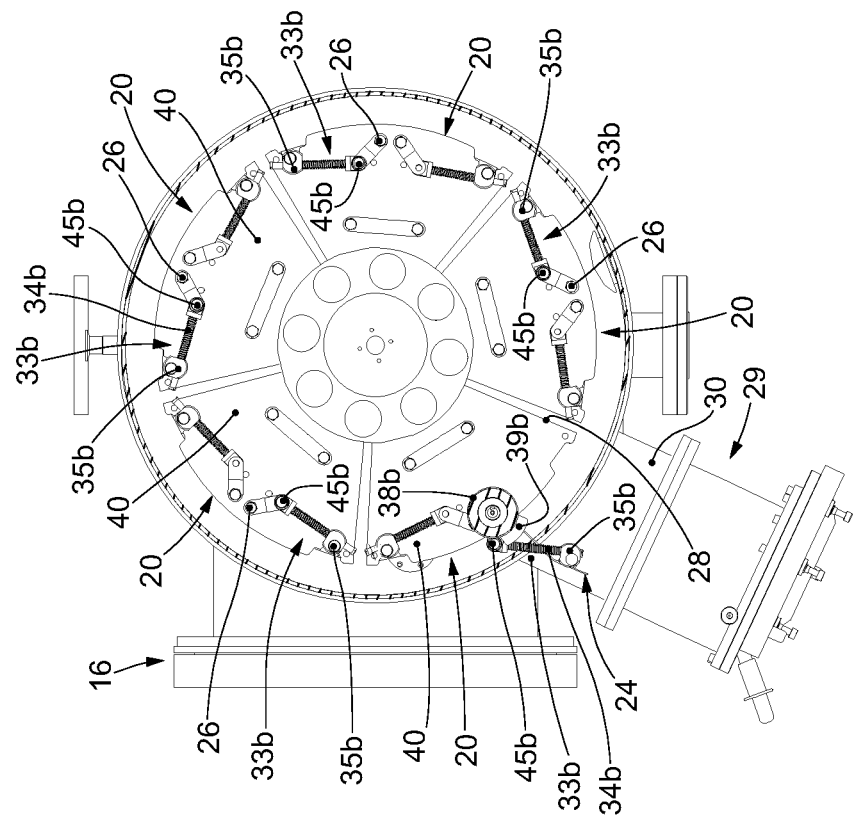
FIG. 6 is another partly sectioned view from the second side of the treatment machine for loose products, during the loading of the loose products to be treated.

FIG. 6 shows a loading door 23 open in correspondence with the loading zone 16 thanks to the rotation and thrust of the drive element 39a of the actuator 38a on the pawl 45a. The thrust of the drive element 39a on the pawl 45a determines a rotation of the arms 34a and 37a around the rotation pin 25. In this step it is possible to introduce the loose products to be treated manually inside the containing device 20, through the loading zone 16, and then to close the loading door 23.

As can be seen, the loading door 23 and the upper wall 27 of the containing device 20 are in a position divergent toward the loading zone 16, so as to facilitate, like a sort of funnel, the insertion of the loose products inside the containing device 20.

When the planned quantity of loose products to be treated has been introduced into the containing device 20 with the loading door 23 open, the containing device 20 is closed by lowering the loading door 23 and the drum 12 is made to rotate, for example in a clockwise direction (see FIG. 7), so that a new, empty containing device 20 is presented in correspondence with the loading zone 16.

The drive element 39a of the actuator 38a will therefore engage the pawl 45a of a subsequent containing device 20, to open its loading door 23.

When the containing devices 20 are all loaded with the planned quantities of loose products, the treatment process can begin, operated by the machine 10 by rotating the drum 12, for example washing and/or sterilization.

Figure 7:
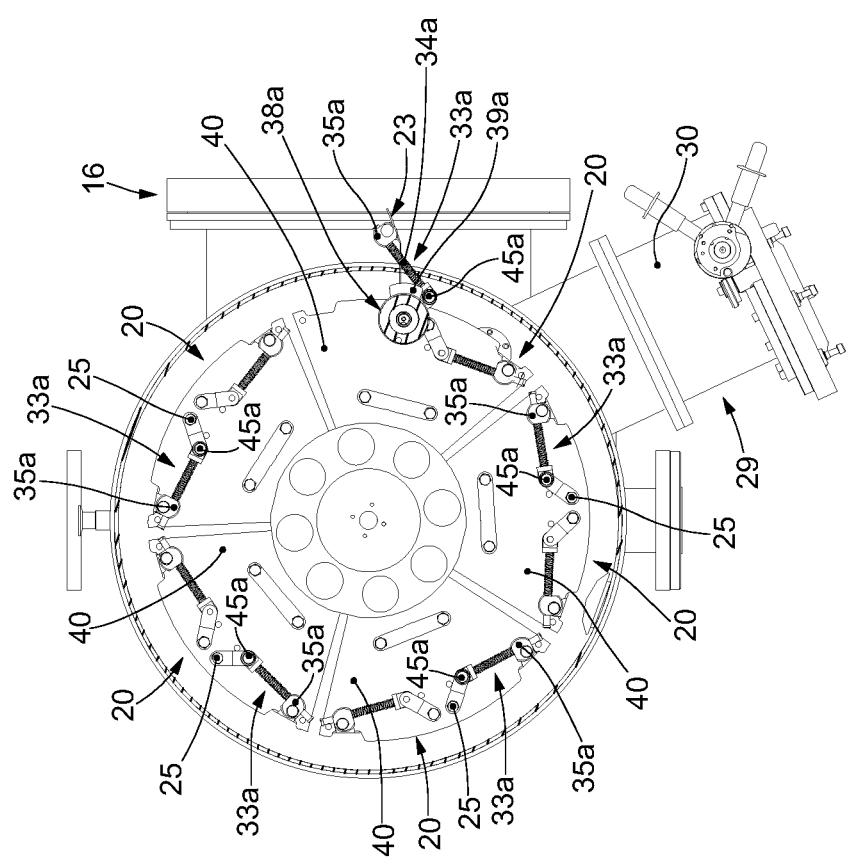
FIG. 7 is another partly sectioned view from the first side of the treatment machine for loose products, during the unloading of the loose products that have been treated.

FIG. 7 and FIG. 3 show an unloading door 24 open in correspondence with the unloading zone 29, thanks to the rotation and thrust of the drive element 39b of the actuator 38b on the pawl 45b. The thrust of the drive element 39b on the pawl 45b determines a rotation of the arms 34b and 37b around the rotation pin 26. In this step it is therefore possible to unload the loose products that have been treated, through the unloading zone 29, from inside the containing device 20 and then to close the unloading door 24 again.

The unloading door 24 shown in the open position in FIG. 7 therefore has a big unloading zone for the loose products to the unloading pipe 30. In fact, as can be seen, the unloading door 24 and the lower wall 28 of the containing device 20 along which the treated loose products slide are divergent toward the unloading zone 29, therefore the loose products that have been treated do not meet any obstacle and descend rapidly and due to gravity toward the unloading zone 29.

When the treatment process is finished therefore, the drum 12 is rotated to present all the containing devices 20 in succession in correspondence with the actuator 38b, so that the respective drive element 39b can engage with the pawls 45b of the opening and closing units 33b of said containing devices 20, so that all the containing devices 20 can be emptied.

Figure 2:
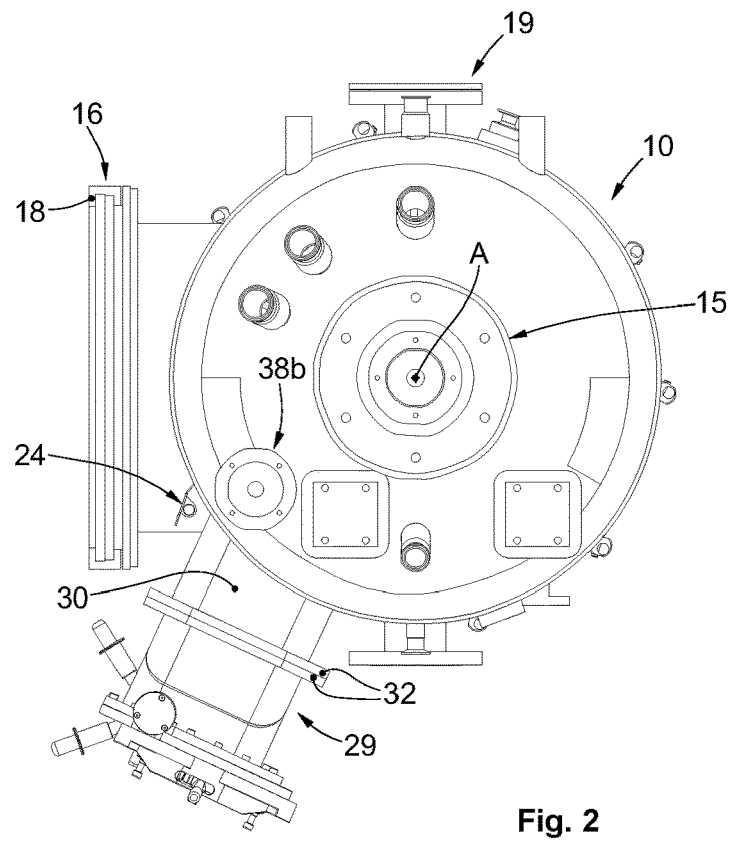
FIG. 2 is a view from a first side of the machine for treating loose products.

The unloading door 24 in the open position is also visible in the three-dimensional view of FIG. 1 and in the lateral view of FIG. 2.

By means of the present containing device 20, it is therefore possible to guarantee effective loading operations of loose products to be treated and unloading operations of loose products that have been treated from the drum 12 by means of a loading door 23 and an unloading door 24 that are positioned on the open side 22 of the containing device 20 and are selectively opened or closed to allow the loading of the loose products to be treated and the unloading of the loose products that have been treated.

In particular, the loading door 23, once open, and the lateral wall of the containing device 20 nearest the loading zone 16, that is, the upper wall 27, have a suitable divergence toward the loading zone 16 so as to facilitate, like a sort of funnel, the loading of the loose products to be treated into the containing device 20.

In particular, the unloading door 24, once open, and the lateral wall of the containing device 20 nearest the unloading zone 29, that is, the lower wall 28, have a suitable divergence toward the unloading zone 29 so as to facilitate the unloading of the loose products that have been treated from the containing device 20.

The containing device 20 with loading and unloading doors 23 and 24 is particularly suitable for use in a machine 10 for treating loose products with a loading zone 16 and an unloading zone 29 situated on the same side of the machine.

It is clear that modifications and/or additions of parts may be made to the containing device for treatment machines for loose products as described heretofore, without departing from the field and scope of the present invention.

It is also clear that, although the present invention has been described with reference to some specific examples, a person of skill in the art shall certainly be able to achieve many other equivalent forms of containing device for treatment machines for loose products, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. A containing device suitable to house loose products in a treatment machine, and comprising: an internal treatment compartment that has two flat and opposite lateral walls, connected by two other lateral, parallel walls,
    wherein said two flat and opposite lateral walls and said two other lateral walls are connected in correspondence with their lower sides by means of a bottom wall and form on their upper sides an open side to load the loose products to be treated and to unload the loose products that have been treated,
    wherein the two flat and opposite lateral walls each lie on a respective opposing plane, the opposing planes on which said two flat and opposite lateral walls lie are reciprocally symmetrical with respect to a central plane, so that said opposing planes and said central plane converge on a line positioned on the other side of the bottom wall with respect to the open side,
    wherein said containing device comprises at least a first loading door for the loose products to be treated, positioned on a first portion of said open side and associated with a first opening and closing unit, and at least a second unloading door for the loose products that have been treated, positioned on a second portion of said open side and associated with a second opening and closing unit,
    wherein the loading door is connected to the containing device by a first rotation pin and the unloading door is connected to the containing device by a second rotation pin separate from and spaced from the first rotation to allow said doors to rotate around their corresponding rotation pins,
    wherein said first and second rotation pins are situated nearer to each other than to any of said flat and opposite lateral walls;
    wherein the loading door and the unloading door, when the containing device is closed, span across all of the open side of the containing device;
    wherein the treatment compartment has a trapezoidal shape and the bottom wall has, in cross section, a smaller extension with respect to the open loading and unloading side;
    wherein, during a loading operation of the loose products, an upper one of the lateral walls and the loading door are divergent toward a loading zone and, during an unloading operation of the loose products, the unloading door and a lower one of the lateral walls are divergent toward an unloading zone;
    wherein the first loading door is rotatable about the first rotation pin, the first opening and closing unit operatively coupling the first rotation pin to the first loading door;
    further wherein the second unloading door is rotatable about the second rotation pin, the second opening and closing unit operatively coupling the second rotation pin to the second unloading door; and
    wherein the first opening and closing unit is connected to the first loading door and is connected to the first rotation pin by a first articulating arm, and wherein the second opening and closing unit is connected to the second unloading door and is connected to the second rotation pin by a second articulating arm.

2. The device as in claim 1, wherein, when the loading door is in an open position, at least one wall of said treatment compartment and the loading door are positioned relative to one another to facilitate insertion of the loose products through a loading zone and into the containing device.

3. The device as in claim 1, wherein, when the unloading door is in open position, at least one wall of said treatment compartment and the unloading door are positioned relative to one another to facilitate descent of the treated loose products toward an unloading zone.

4. The device as in claim 1, wherein said first and second rotation pins are situated in proximity to the central plane of the containing device.

5. The device as in claim 1, wherein the opening and closing unit of the loading door comprises at least a protruding pawl associable with an actuator to drive said opening and closing unit of the loading door.

6. The device as in claim 1, wherein the opening and closing unit of the unloading door comprises at least a pawl protruding and suitable to engage with an actuator to drive said opening and closing unit of the unloading door.

7. A machine to treat loose products, comprising a treatment chamber in which a rotatable drum is housed, a loading zone for loading the loose products to be treated and an unloading zone for unloading the treated loose products, wherein the loading zone and unloading zone are positioned on the same side of the machine, said drum comprising a plurality of containing devices, and wherein each containing device is a containing device as recited in claim 1.

8. The machine as in claim 7, wherein the machine is for washing and/or sterilizing objects.

9. The machine as in claim 7, wherein the loading door and the unloading door of each containing device are rotatable around corresponding rotation pins directed parallel to an axis of rotation of the drum.

10. The device as in claim 1, wherein
    the opening and closing unit of the loading door is mounted externally to a first one of the parallel lateral walls of the containing device and includes a first protruding pawl arranged to respond to a first actuator to drive the opening and closing unit of the loading door; and
    wherein the opening and closing unit of the unloading door is mounted externally to a second one of the parallel lateral walls and comprises a second protruding pawl arranged to respond to a second actuator to drive the opening and closing unit of the unloading door.

11. A method for treating loose products in a treatment machine for loose products, said machine comprising a treatment chamber in which a rotatable drum is housed, a loading zone for loading loose products to be treated and an unloading zone for unloading treated loose products, wherein the loading zone and the unloading zone are positioned on the same side of the machine, said drum comprising a plurality of containing devices, wherein each containing device is a containing device as recited in claim 1, the method comprising: loading loose products to be treated in each of the containing devices through a loading door positioned on a first portion of an open side of each of the containing devices, treating loose products in the containing devices by rotating the drum, and unloading loose products that have been treated from each of said containing devices by means of an unloading door positioned on a second portion of said open side of each of the containing devices.

12. A containing device suitable to house loose products to be treated in a treatment machine and comprising:
   an internal treatment compartment that has two flat and opposite lateral walls, connected by two other parallel lateral walls,
   wherein lower sides of said two flat and opposite lateral walls and said two other parallel lateral walls are connected to a bottom wall, and form on upper sides an open side to load the loose products to be treated and to unload loose products that have been treated,
   wherein the two flat and opposite lateral walls each lie on a respective opposing plane, the opposing planes on which said two flat and opposite lateral walls lie are reciprocally symmetrical with respect to a central plane, so that said opposing planes and said central plane converge on a line positioned on the other side of the bottom wall with respect to the open side,
   the containing device further includes a first door for receiving the loose products to be treated, the first door positioned on a first portion of said open side and associated with a first respective opening and closing unit, and a second door for unloading loose products that have been treated, the second door positioned on a second portion of said open side and associated with a second respective opening and closing unit,
   wherein the loading door is connected to the containing device by a first rotation pin and the unloading door is connected to the containing device by a second rotation pin different from and non-coaxial from the first rotation pin to allow said doors to rotate around their respective rotation pin,
   wherein said first and second rotation pins are situated nearer to each other than to any of said flat and opposite lateral walls; and
   wherein each of the loading door and the unloading door span the whole extent of a distance between the two other parallel lateral walls and together span the whole extent of a distance between the two flat and opposite lateral walls to thereby cover all of the open side when closed; and
   wherein the first door is rotatable about the first rotation pin, the first opening and closing unit having a first articulating arm operatively coupling the first rotation pin to the first door; and
   further wherein the second door is rotatable about the second rotation pin, the second opening and closing unit having a second articulating arm operatively coupling the second rotation pin to the second door.

13. The device as in claim 12, wherein:
   the opening and closing unit of the loading door is mounted externally to a first one of the parallel lateral walls of the containing device and includes a first protruding pawl arranged to respond to a first actuator to drive the opening and closing unit of the loading door; and
   wherein the opening and closing unit of the unloading door is mounted externally to a second one of the parallel lateral walls and comprises a second protruding pawl arranged to respond to a second actuator to drive the opening and closing unit of the unloading door.

14. A machine to treat loose products, the machine comprising:
   a treatment chamber;
   a loading zone for loading loose products to be treated;
   an unloading zone for unloading products that have been treated; and
   a rotatable drum housed in the treatment chamber, wherein the rotatable drum comprises a plurality of containing devices;
   wherein each containing device comprises:
   an internal treatment compartment that has two flat, opposite lateral walls connected by two other lateral, parallel walls;
   wherein each wall of the two flat, opposite lateral walls and the two other lateral, parallel walls comprises a lower side and an upper side;
   wherein said two flat, opposite lateral walls and said two other lateral, parallel walls are connected-by means of a bottom wall, and wherein the upper sides of the two flat, opposite lateral walls and the upper sides of the two other lateral, parallel walls form a loading and unloading side to load the loose products to be treated and to unload the loose products that have been treated;
   wherein the two flat, opposite lateral walls lie on respective opposing planes, the opposing planes on which said two flat, opposite lateral walls lie are reciprocally symmetrical with respect to a central plane, so that said opposing planes and said central plane converge on a line positioned on the other side of the bottom wall with respect to the-loading and unloading side;
   a loading door for the loose products to be treated, positioned on a first portion of said loading and unloading side and directly connected to a first opening and closing unit, and an unloading door for the loose products that have been treated, positioned on a second portion of said loading and unloading side and directly connected to a second opening and closing unit;
   wherein the first opening and closing unit comprises a protruding pawl configured to engage with an actuator of the machine to drive the first opening and closing unit and wherein the second opening and closing unit comprises a protruding pawl configured to engage with an actuator of the machine to drive the second opening and closing unit;
   wherein the loading door is connected to its respective containing device by first rotation pins and the unloading door is connected to its respective containing device by second rotation pins separate from and spaced from the first rotation pins to allow said doors to rotate around their corresponding rotation pins; and
   wherein the first rotation pins are situated nearer to the second rotation pins than to either of the flat, opposite lateral walls, and wherein the second rotation pins are situated nearer to the first rotation pins than to either of the flat, opposite lateral walls.

15. A machine to treat loose products, the machine comprising:
   a treatment chamber;
   a loading zone for loading loose products to be treated;
   an unloading zone for unloading products that have been treated; and
   a rotatable drum housed in the treatment chamber, wherein the rotatable drum comprises a plurality of containing devices;

wherein each containing device comprises:

an internal treatment compartment that has two flat and opposite lateral walls connected by two other parallel lateral walls;

wherein each wall of the two flat and opposite lateral walls and the two other parallel lateral walls comprises a lower side and an upper side;

wherein the lower sides of said two flat and opposite lateral walls and the two other parallel lateral walls are connected to a bottom wall, and wherein the upper sides of the two flat and opposite lateral walls and the upper sides of the two other parallel lateral walls form a loading and unloading side to load the loose products to be treated and to unload the loose products that have been treated;

wherein the two flat and opposite walls lie on respective opposing-planes, the opposing planes on which said two flat and opposite walls lie are reciprocally symmetrical with respect to a central plane, so that said opposing planes and said central plane converge on a line positioned on the other side of the bottom wall with respect to the loading and unloading side;

a loading door for receiving the loose products to be treated, the loading door positioned on a first portion of said loading and unloading side and directly connected to a first opening and closing unit, and an unloading door for unloading the loose products that have been treated, the unloading door positioned on a second portion of said loading and unloading side and directly connected to a second opening and closing unit;

wherein the first opening and closing unit comprises a protruding pawl configured to engage with an actuator of the machine to drive the first opening and closing unit and wherein the second opening and closing unit comprises a protruding pawl configured to engage with an actuator of the machine to drive the second opening and closing unit;

wherein the loading door is connected to its respective containing device by first rotation pins and the unloading door is connected to its respective containing device by second rotation pins different from and non-coaxial from the first rotation pins to allow said doors to rotate around their respective rotation pins; and wherein the first rotation pins are situated nearer to the second rotation pins than to either of the flat and opposite lateral walls, and wherein the second rotation pins are situated nearer to the first rotation pins than to either of the flat and opposite lateral walls.

\* \* \* \* \*